United States Patent
Treaba et al.

(10) Patent No.: US 6,421,569 B1
(45) Date of Patent: Jul. 16, 2002

(54) COCHLEAR IMPLANT ELECTRODE ARRAY

(75) Inventors: Claudiu-Gheorghe Treaba, Wollstonecraft; Fysh Dadd, Leichhardt; Derek Ian Darley, Cromer Heights; John L. Parker, Roseville, all of (AU)

(73) Assignee: Cochlear Limited, Lane Cove (AU)

(*) Notice: Subject to any disclaimer, the term of this patent is extended or adjusted under 35 U.S.C. 154(b) by 0 days.

(21) Appl. No.: 09/454,976

(22) Filed: Dec. 3, 1999

(30) Foreign Application Priority Data

May 21, 1999 (AU) .................. PCT/AU99/00391

(51) Int. Cl.⁷ .................................. A61N 1/05
(52) U.S. Cl. ............................. 607/137; 607/57
(58) Field of Search ................. 607/137, 55–57

(56) References Cited

U.S. PATENT DOCUMENTS

| | | | |
|---|---|---|---|
| 4,284,857 A | 8/1981 | Slavin et al. | 381/394 |
| 4,357,497 A * | 11/1982 | Hochmair et al. | 607/137 |
| 4,686,765 A | 8/1987 | Byers et al. | |
| 4,898,183 A | 2/1990 | Kuzma | 607/137 |
| 5,123,422 A | 6/1992 | Charvin | 607/137 |
| 5,545,219 A | 8/1996 | Kuzma | 623/10 |
| 5,645,585 A | 7/1997 | Kuzma | 623/10 |
| 5,653,742 A | 8/1997 | Parker et al. | 607/137 |
| 5,653,743 A | 8/1997 | Martin | 623/1.35 |
| 5,667,514 A | 9/1997 | Heller | 606/108 |
| 5,999,859 A * | 12/1999 | Jolly | 607/137 |
| 6,070,105 A * | 5/2000 | Kuzma | 607/137 |
| 6,125,302 A * | 9/2000 | Kuzma | 607/137 |

FOREIGN PATENT DOCUMENTS

| | | | |
|---|---|---|---|
| EP | 0002068 A2 | 5/1979 | A61N/1/04 |
| WO | WO 89/00870 | 2/1989 | |
| WO | WO 97/10784 | 3/1997 | |
| WO | WO 97/26943 A1 | 7/1997 | A61N/1/36 |

OTHER PUBLICATIONS

IEEE Transactions on Biomedical Engineering, vol. BME–27, No. 1, (Jan. 1980), 44–50pp; An Eight Channel Scala Tympani Electrode for Auditory Prostheses; by Ingeborhg J Hochmair–Desoyer and Erwin S Hochmair.

* cited by examiner

Primary Examiner—Carl Layno
(74) Attorney, Agent, or Firm—Gottlieb, Rackman & Reisman, P.C.

(57) ABSTRACT

An electrode array for a cochlear implant is formed with a carrier made, for example from silicone, is preshaped and is formed with a lumen. The array is shaped to assume a first. The array can be straightened, and held in a straight configuration by inserting a stylet into the lumen. The array relaxes to a shape matching the curvature of the cochlea when the lumen is removed. The electrodes of the array are disposed on one side of the array to face the modiolus when the array is inserted into the cochlea.

42 Claims, 6 Drawing Sheets

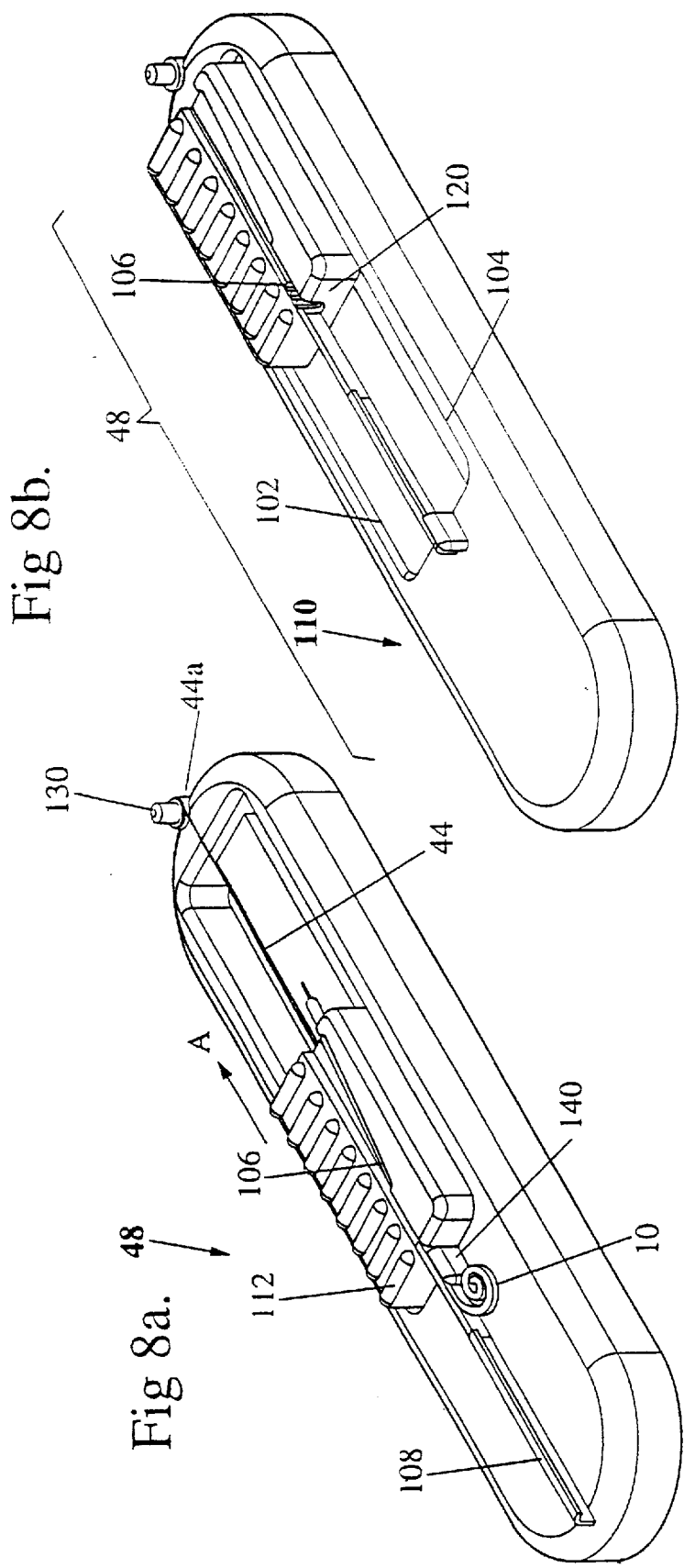

COCHLEAR IMPLANT ELECTRODE ARRAY

FIELD OF INVENTION

This invention pertains to cochlear electrode arrays shaped to a predetermined curvature, and more particularly to a cochlear electrode array which has a first preselected shape suitable for insertion into the body of a patient, and a second shape suitable for providing a specific function, or stimulus.

BACKGROUND OF THE INVENTION

Cochlear implant systems are used to aid patients having a hearing deficiency. More particularly, these systems include a microphone receiving ambient sounds and converting the sounds into corresponding electrical signals, signal processing means of processing the electrical signals and generating cochlea stimulating signals and an electrode array for applying the cochlea stimulating signals to the cochlea of the patient. It is known in the art that the cochlea is tonotopically mapped. In other words, the cochlea can be partitioned into regions, with each region being responsive to signals in a particular frequency range. This property of the cochlea is exploited by providing the electrode array with a plurality of electrodes, each electrode being arranged and constructed to deliver a cochlea stimulating signal within a preselected frequency range to the appropriate region. The electrical currents and electric fields from each electrode stimulate the auditory nerve cells disposed in the modiolus of the cochlea. Several electrodes may be active simultaneously.

It has been found that in order for these electrodes to be effective, the required magnitude of the currents flowing from these electrodes is a function of the distance between the electrodes and the modiolus. If this distance is great, the threshold stimulation current magnitude must be larger than if the distance is smaller. Moreover, the current from each electrode may flow in all directions, resulting in the area of the cochlea stimulated by a single electrode being undesirably large. Therefore the electrical stimulation is not well localised to a particular site on the cochlea. In order to reduce the threshold stimulation amplitude and to improve localisation, it is advisable to keep the distance between the electrode array and the modiolus as small as possible. This is best accomplished by providing an electrode array having a shape which generally follows the shape of the modiolus. In contrast during insertion, the electrode array should be generally straight, because otherwise the insertion procedure is too cumbersome and difficult. Consequently there is a problem due to the hitherto conflicting design objectives that the electrode array be straight during insertion but curved during use.

Several methods and means of curving the electrode array and therefore overcoming the above-described problem have been attempted. These attempts fall generally in two categories. The first category consists of arrays that are formed in a straight configuration, and are mechanically manipulated into a curved configuration by an external device which exerts pressure against the outside wall of the cochlea. These arrays are designed so that part of the array is pressed against the outside wall of the cochlea, and another part is thereby pressed against the inside wall. These types of arrays may be of a two-part design (such as commonly assigned U.S. Pat. Nos. 5,645,585 and 5,545,219,) or they may be of a space-filling design. Both share the disadvantage of exerting a permanent pressure against both the inside and outside wall of the cochlea. The space-filling designs have an additional disadvantage that they displace the cochlear fluid, which may have adverse affects on the patient.

The second category consists of arrays which are shaped into a curved configuration and are then straightened for insertion. Examples of arrays falling into this second category include an electrode array having an electrode carrier provided with a longitudinal element arranged on one side of the carrier which is constructed to change its dimension once the array is inserted. For example, the longitudinal element could include a hydrogel such as PAA (Polyacrylic Acid) which expands after insertion by absorbing water from the cochlear fluid, as described in commonly assigned U.S. Pat. No. 5,578,084. Alternatively, the longitudinal element could be a bimetallic filament (such as nickel/titanium filament) which is shaped to allow the electrode carrier to take a straight configuration at room temperature but bends into a preselected shape once it is exposed to body temperature.

Commonly assigned U.S. Pat. No. 5,653,742 discloses another electrode array falling into the second category. In this patent, the array is encapsulated into a stiffening sheath which holds the array in a linear configuration. The sheath is made of a biosorbable material such as polyvinyl alcohol (PVA) which dissolves in the cochlear fluid after insertion.

While the arrays from this second category remove the disadvantage of the static pressure against the walls of the cochlea, they have other disadvantages in that the surgeon cannot control the point in the surgical procedure at which the array curves, and the array cannot be restraightened during surgery to allow a second attempt at insertion if the first attempt fails.

OBJECTIVES AND SUMMARY OF THE INVENTION

In view of the above-mentioned disadvantages of the prior art, it is an objective of the present invention to provide a cochlear electrode array which has a first, relatively straight configuration so that it can be readily implanted, using a stylet which, after insertion is readily removed and a second, curved configuration to conform to the cochlea of a patient.

A further objective is to provide an array which is small relatively in cross-sectional area, so as to facilitate insertion and minimise the displacement of the cochlea fluid.

Another objective is to provide an array which can be manufactured relatively easily and inexpensively.

Other objectives and advantages of the invention shall become apparent from the following description.

Briefly, an electrode array in accordance with this invention includes an elongated carrier which supports a plurality of electrodes suitable for defining an electrode array for application for cochlear stimulation signals, and wires attached to the electrodes to provide cochlear stimulation signals in the usual manner. The carrier is preferably pre-shaped into a curved configuration selected to insure that the electrodes are disposed in close proximity to the modiolus of the scala tympani. Importantly, the carrier is formed with a lumen which is designed to accept one or more surgical stylets. Prior to insertion of the carrier into the cochlea, the stylet is introduced into the carrier to insure that the carrier is maintained in a substantially straight configuration. As the array is inserted into the cochlea, the stylet is slowly withdrawn allowing the array to assume a curved configuration. Preferably the stylet is relatively stiff along its entire length except for its tip. The tip is annealed to render it more malleable then the rest of the stylet to allow the array to flex easily as it is being inserted.

Preferably, the electrodes are disposed on an inner surface of the carrier, so that when the carrier is implanted, the electrodes are facing the modiolus. Each electrode may be formed from a ring with a wire threaded through the ring, the ring then being collapsed into a U-shaped electrode element to grip the wire. The electrodes and wires are then embedded into the carrier.

Several methods for producing the electrode array can be used. For example, a blank may be formed around a curved production stylet, and the stylet may be withdrawn from the blank to form a lumen. The electrodes and their wires are attached to the blank and a moulding material is applied to complete the carrier.

After the carrier and its electrodes are completed, it may be packaged in its curved configuration together with an appropriate surgical stylet, and a straightening jig. Prior to surgery, the straightening jig is used to simultaneously straighten the carrier and insert the stylet into the lumen of the carrier. The stylet is stiffer and more rigid than the carrier so that once the stylet is inserted into the lumen, the electrode array can be removed from the jig with the carrier maintaining its straight configuration for insertion.

BRIEF DESCRIPTION OF THE DRAWINGS

FIG. 1b shows a side elevational view of the electrode array of FIG. 1a;

FIG. 2b shows an enlarged cross sectional view of the array taken along lines II—II in FIG. 2a;

FIGS. 8a and 8b show an orthogonal view of a jig used to straighten the array prior to surgery.

DETAILED DESCRIPTION OF THE INVENTION

Figure 1A:
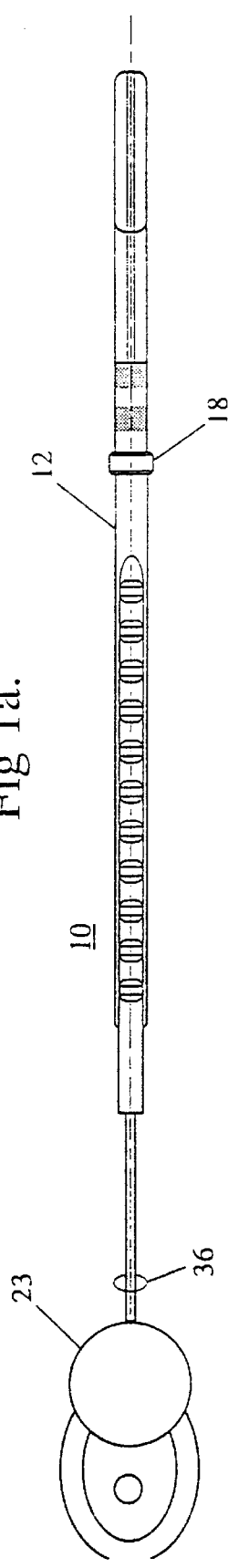
FIG. 1a shows a plan view of a cochlear implant array constructed in accordance with this invention in a relaxed state.

A preferred embodiment of the invention shall now be described in conjunction with the figures. Starting with FIGS. 1a–1c, an electrode array 10 constructed in accordance with this invention is shown in a state wherein it follows the natural curvature of the cochlea of an adult.

This electrode array consists of an elongated carrier 12 having a straight portion 14 and a portion 16 which has a spiral shape. Portion 16 subtends an arc of about 450°, as shown. The array 10 is provided with a plurality of electrodes shown in FIGS. 2a, 2b and described below. These electrodes have been omitted from FIGS. 1a–c for the sake of clarity. The carrier 12 is made of a plastic material, such as medical grade silicone rubber, as described in more detail below.

Portion 14 is provided with a ring 18 to indicate insertion depth, especially during extraction of the stylet (described below). The ring 18 is used for holding the array 10 during the insertion. From the ring 18, portion 14 widens slightly to form two tubes 22 and 24. Tube 22 is formed of a plurality of longitudinally spaced external ribs 26, provided to allow fixation using bone cement or platinum ties (not shown). Tube 22 holds a plurality of wires 36 discussed below which extend from the receiver/stimulator 23 to the electrodes of portion 16. Tube 24 encloses a lumen 30 which extends through the length of electrode 10. Lumen 30 is fabricated using a production stylet 31, and is used to house a surgical stylet 44, as described below.

Figure 2A:
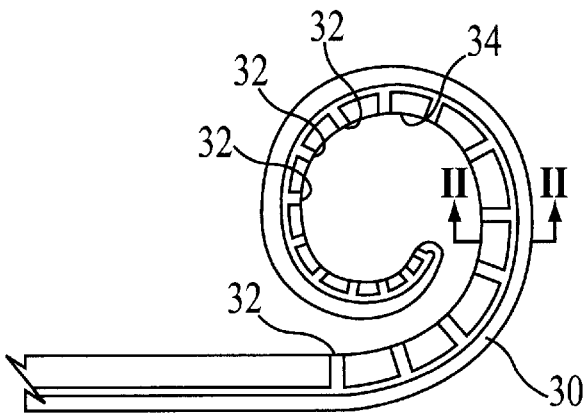
FIG. 2a shows an enlarged cross sectional view of the distal end of the electrode array of FIGS. 1a–c.
Figure 2B:
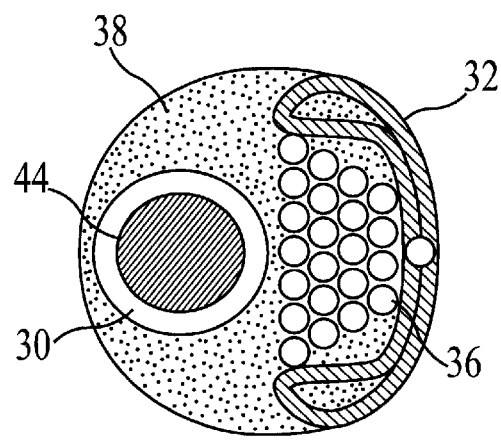
Figure 3:
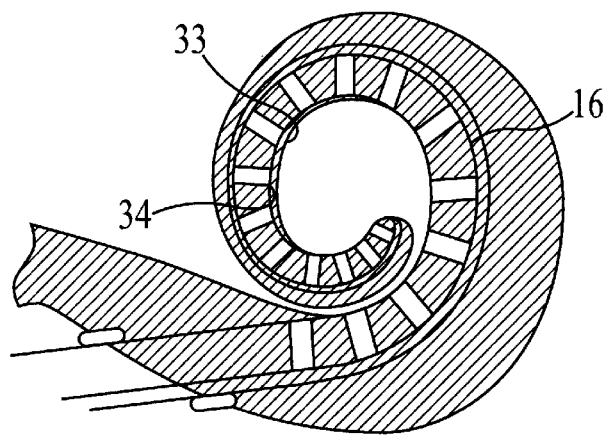
FIG. 3 shows a somewhat diagrammatic view of a cochlear array as it is inserted into the cochlea.

Referring now to FIGS. 2a and 2b, portion 16 has a plurality of electrodes 32 arranged on an inner surface 34, i.e., the surface facing the modiolus 33, as shown in FIG. 3. Each electrode 32 is connected to one or more wires 36. Advantageously the electrodes 32 form a channel for the wires 36 connected to the electrodes 32. The electrodes 32 and wires 36 are embedded in the plastic material 38 forming the carrier 12.

Figure 4A:
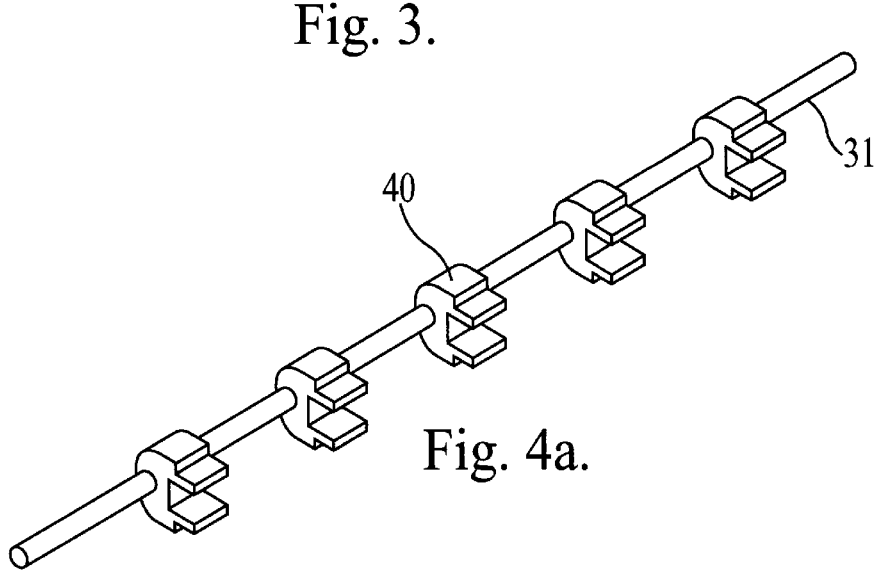
FIG. 4a shows a production stylet with spacers used to make a blank.
Figure 4B:
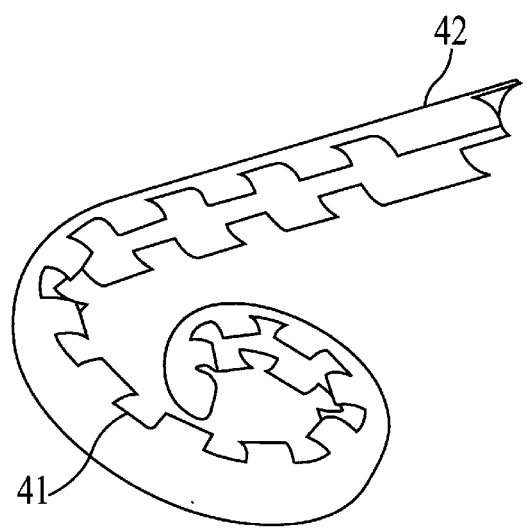
FIG. 4b shows a blank being formed.

With reference to FIGS. 4a–4d, a method of making the array 10 is now described. First, the production stylet 31 is cut to size from platinum wire coated with polytetrafluoroethene i.e. "teflon". A plurality of donut shaped spacers 40 made of silicone are inserted over the production stylet 31 as seen in FIG. 4a. Importantly at its tip 31A, (FIG. 4c) the teflon coating is removed from the production stylet 31 thereby forming the narrow section at the end of the lumen. Next, the stylet 31 with the spacers 40 is inserted into a curved die (not shown) and a silicone material is poured into the curved die and cured to form a moulded blank 42 which includes the production stylet 31 and the spacers 40 embedded therein. The spacers 40 insure that the production stylet is positioned at a predetermined location within the moulded blank 42. The die is shaped to insure that the blank 42 has an end section 16A which is not curved but is formed so that it is relatively straight. This section 16A may have a length of about 0.7 mm. The bare tip 31A of production stylet 31 is disposed in this end section 16A. After the moulded blank 42 is cured, it is removed from the die. The production stylet is then withdrawn from the moulded blank 42 leaving behind the lumen 30 having a tip 30A which is narrower then the rest of the lumen. The spacers 40 are also left behind on removal of the production stylet. The non-stick property of the teflon facilitates the easy removal of production stylet 31 from the cured silicon array, thereby leaving a smooth lumen 30 behind. Prior to the removal of the molded blank from the moulding die, the lumen 30 is, of course, circular.

In a separate operation a plurality of electrodes 32 are formed and attached to corresponding wires 36 as follows. First several rings made of platinum are provided. A typical array may have 22 electrodes in which case the following sized rings may be used: 6 rings with an outer diameter of 0.6 mm, 6 rings with an outer diameter of 0.63 mm and 10 rings with an outer diameter of 0.65 mm.

A parylene-coated Pt/Ir wire is connected to each of the rings as follows. The wire is placed inside the ring and welded, and then the ring is then collapsed and welded also, using a welding electrode to form a U-shaped electrode 32 shown in FIG. 4d. The wire 36 extends away from the electrode 32.

Generally, every electrode 32 is connected in this manner to a single wire 36. However, with the technique described above it is relatively easy to connect two or more wires, such as wire 36A, to each electrode 32 as well. Multiple wires provide redundancy in case one of them breaks, and importantly, also provide greater mechanical flexibility for a given electrical resistance.

Figure 5:
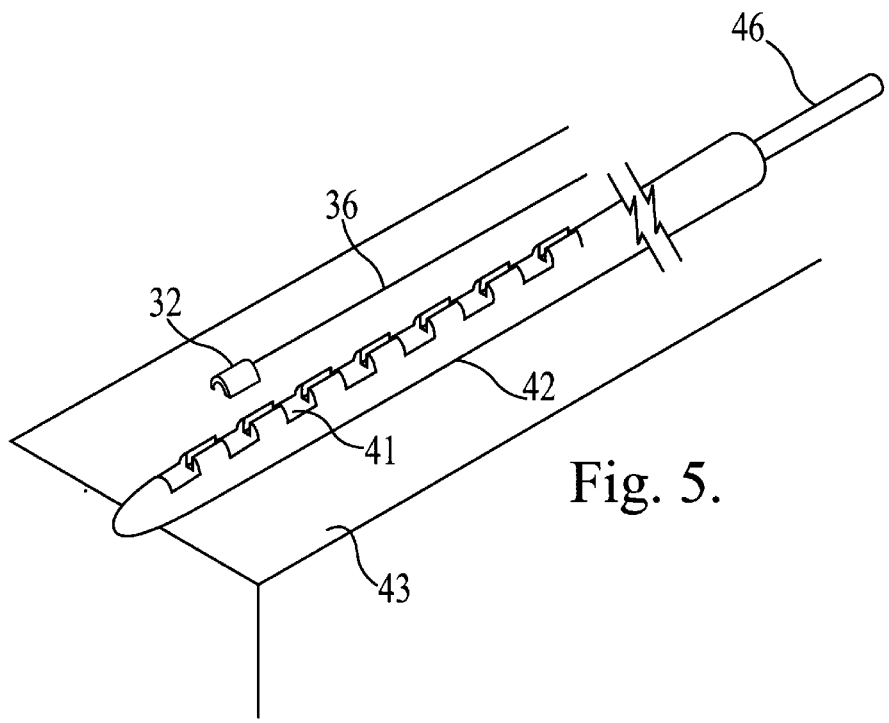
FIG. 5 shows an alternate technique of making the array.
Figure 4D:
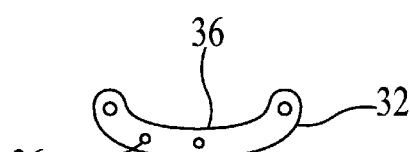
FIG. 4d shows a side view of an electrode ring.
Figure 6:
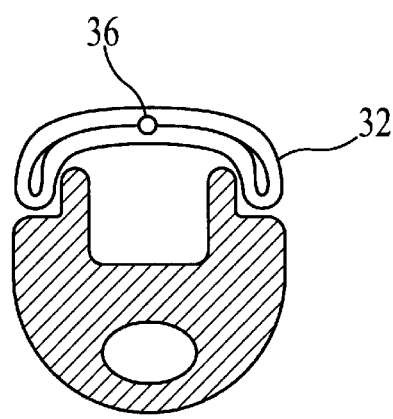
FIG. 6 shows in cross-section the attachment of an electrode ring to a blank.

The moulded blank 42 is next manually straightened and placed into a production jig 43 adapted to hold the moulding blank 42 in the straight configuration (FIG. 5). The production jig preferably comprises a flat piece of chrome-plated brass with indents to hold the electrodes in correct position for attachment to the production stylet. In this configuration a second production stylet 46 is inserted into the lumen 30 to hold the moulded blank 42 straight. The second production stylet 46 is straight, and preferably is made of stainless steel. Once the second production stylet 46 has been fully inserted into the lumen 30, the production jig 43 is removed. Next, each of the electrodes 32 is glued in one of the recesses 41 on the blank 42 as shown in FIG. 5, using a dab of silicone. Recesses 41 are formed by the shape of the die used to mould the blank. The blank 42 is then backfilled with a silicone filler material and the whole array is cured to complete the array 10. Upon addition of the silicon filler material and curing spacers 40 and the added filler amalgamate to form an homogeneous whole. The second production stylet 46 is then removed.

The array may alternatively be fabricated by the following method. A set of electrodes are formed by pressing rings of platinum into a U-shape. The electrode furthest from the tip of the electrode array is placed in a straight welding die (not shown), where a wire is welded to that ring. A droplet of silicone is placed in the trough of the electrode. A second electrode is then placed in the welding die, and a wire is welded to it. The wire from the second electrode is bedded down into the silicone droplet in the trough of the first electrode. A droplet of silicone is then placed in the trough of the second electrode. A third and subsequent electrodes are placed in a similar fashion. Additional droplets of silicone may be placed in the earlier electrodes if necessary to capture all of the wires.

Once all of the electrodes have been welded and assembled in the straight welding die the production stylet is pressed on top of the wires and silicone in the troughs of the electrodes. Each electrode trough is then partially filled with more silicone. The whole assembly is then placed in an oven to cure the silicone.

The assembly is then removed from the straight die and carefully curved to match the shape of a curved moulding die. The assembly is then placed in the curved moulding die and the space in the die is packed with silicone material. A matching die cover is placed over the assembly and pressed down. The die is then placed in an oven to cure the silicone. The die is then open to allow the resulting electrode array to be removed from the die.

The array 10 may alternatively be fabricated by placing a production stylet 31, U-shaped electrodes 32 and wires 36 into a curved moulding die (not shown). The electrodes are placed in the die one at a time, starting at the base, with the wire from each electrode passing through the trough formed by the previously inserted electrodes. Once all of the electrodes 32 have been placed in the die the whole space is packed with silicone material, and a matching die cover is placed over and pressed down over the moulding die. The array is cured, and then removed from the die, and the production stylet removed from the array.

After completion, the array 10 is attached to the cochlear implant receiver/stimulator 23 in the same fashion as prior art electrode arrays.

The assembly formed of the array 10 and the receiver/stimulator 23 is packaged and shipped in an electrode array kit which also includes a surgical stylet 44 and, optionally, a straightening jig 48.

The surgical stylet 44 is formed from an uncoated wire of a malleable, biocompatible wire such as platinum, having a diameter of about 0.125 mm. A length of wire of about 3 mm forms the tip of the surgical stylet 44 is annealed to thereby making it more flexible. The opposite end of stylet 44 is curved to form a loop 44A to allow the manipulation of the stylet 44.

The straightening jig 48 shown in FIGS. 8a and 8b is used to straighten the array 10 prior to surgery as shall now be described. The jig 48 contains a fixed platform 110 and a moving carriage 120 which can slide on platform 110 along a pair of rails 102, 104. Platform 110 is also provided with a pin 130 disposed at one end of the platform 110 as shown. Also attached to the platform is a stationary wall 140.

The carriage 120 is formed with a trough 106 extending longitudinally through the carriage 120. On one side of this trough 106, the carriage 120 is provided with an extension 108 disposed in parallel with and adjacent to stationary wall 140 as shown. The carriage 120 also has a top surface with ribs 112 which allow a person to move the carriage 120 on top of platform 110.

Before surgery, the array 10 is positioned on platform 110 so that the portion 16 is disposed adjacent to the stationary wall 140 and the portion 14 extends between the stationary wall 140 and the extension 108 and into the trough 106. In this position, the portion 14 of the array 10 is captured by the carriage 120.

Surgical stylet 44 is positioned so that its tip is inserted into the lumen 30 while the remainder of the stylet 44 extends from the carriage 120 to the pin 130 with the loop 44A being fitted over the pin 130 as shown in FIG. 8a. The array is now ready to be straightened.

Because the carriage 120 grips the electrode array 10, as the carriage 120 is moved in the direction of arrow A in FIG. 8a, the portion 16 of the array 10 is forced to unravel slowly between the stationary wall 140 and extension 108. Simultaneously with the unravelling or straightening of portion 16, the array 10 is pulled over the surgical stylet 44 like a stocking. Once the array 10 is fully straightened the stylet 44 is fully inserted into lumen 30, and the straightened array 10 with stylet 44 in place can be removed from the jig 48.

Preferably, the straightening jig 48 is packed with the electrode array 10, with the surgical stylet 44 being partially inserted into tube 24 of array 10. This allows the array 10 to be stored with the portion 16 in its moulded state, yet is ready to be easily straightened by the surgeon just prior to use.

In an alternate embodiment, the array 10 is straightened prior to shipment using the straightening jig 48, and the surgical stylet 44 is inserted to hold the array 10 straight. In this embodiment the kit shipped to the surgeon need not include the jig 48 since it is not necessary. However, this alternative may be less desirable since the array 10 may be in the straight configuration for a relatively long time period and may lose its curved natural or relaxed shape.

Figure 2C:
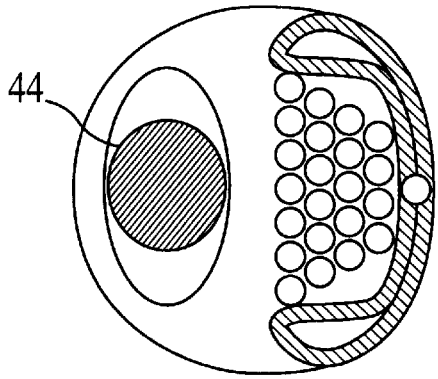
FIG. 2c is similar to FIG. 2b and shows the straightened array holding the surgical stylet in place.

The surgical use of a cochlear implant utilising the inventive electrode array 10 will now be described. First, the array 10 is straightened and held in this configuration using jig 48. Simultaneously the surgical stylet 44 is fully advanced into lumen 30 as described above and in FIGS. 8*a* and 8*b*. With the array 10 straight, the lumen 30 assumes a tight oval cross-sectional shape which grips the surgical stylet so that it will not easily fall out, as shown in FIG. 2*c*.

In the following description it is assumed that the surgeon is now ready to insert the array 10 into the patient's cochlea.

As described above, the end 31A of production stylet 31 is narrower than the rest of the stylet 31. Therefore the resulting lumen 30 has a narrower end 30A as well. When the surgical stylet 44 is inserted into the lumen 30, its tip is wedged into and forms in interference fit with the end 30A of the lumen 30 so that the surgical stylet 44 is retained in the lumen 30 until it is forcibly removed. As previously mentioned, this tip is annealed to make it softer then the rest of the stylet 44.

After the surgical stylet 44 is fully inserted into the lumen 30, the array 10 and stylet 44 are removed from the jig 48 and the jig is discarded. (Of course, if the array 10 is shipped with the surgical stylet 44 in place, this step is omitted).

Figure 7A:
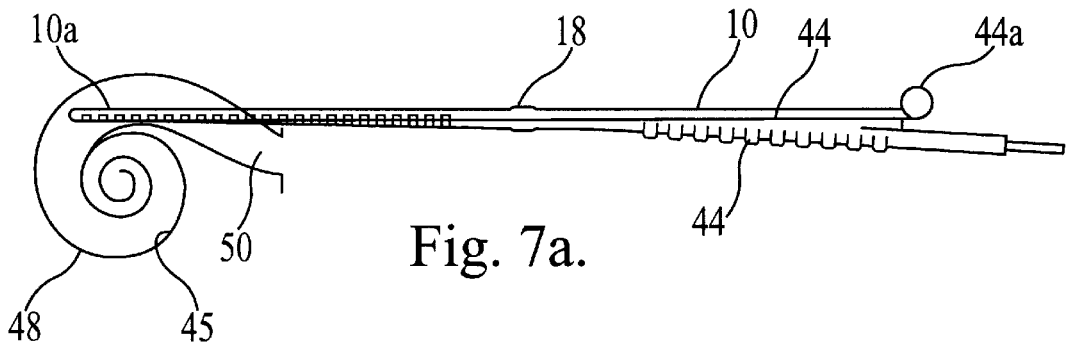
FIGS. 7a–7d show the electrode array being inserted into the cochlea.
Figure 7B:
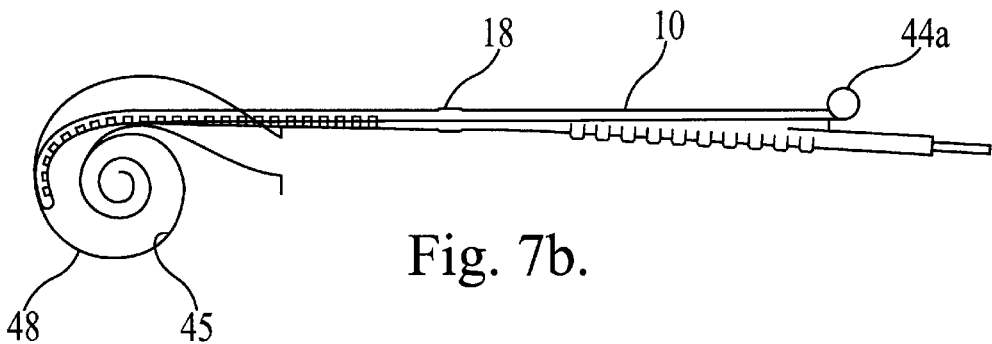
Figure 7C:
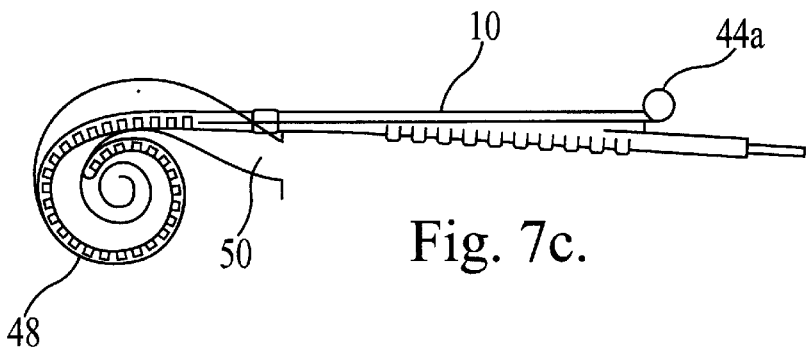

Referring now to FIGS. 7*a*–7*d*, a surgeon inserts the array 10 as follows. First, he makes an incision in the cochlea 48 in a normal fashion to generate a small access 50 in its sidewall. The surgeon inserts the tip 10 A of the array 10 through the access 50 slowly. (FIG. 7*b*) As the array 10 is introduced, it starts curving to follow the curvature of the outer wall 45 of the cochlea until the final position shown in FIG. 7*c* is reached. The insertion is made easier because the array has no electrodes along the outside surface, just a smooth surface of silicone. This minimises friction between the array 10 and the outer wall 45 of the cochlea. The friction is also reduced because the stylet is made of a malleable material. Therefore the array 10 with the stylet 44 inside conforms to the shape of the outer wall 45 cochlea without applying any substantial static outward pressure as would be the case if the stylet 44 was in elastic deformation.

The insertion is further assisted by the straight preferred feature portions on the tips of the array 10 and stylet 44, respectively, which help to prevent the array 10 from folding over.

Figure 7D:
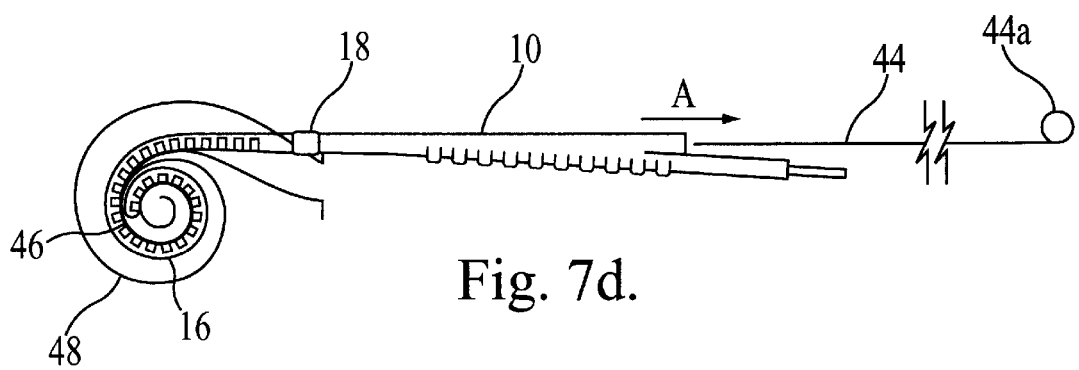

During the insertion, the surgeon can judge the position of the array 10 within the cochlea by the relative positions of the mark 18. When the mark 18 reaches the access hole 50, the surgeon knows that the final position of the array 10 has been reached. At this point the surgeon removes and discards the surgical stylet 44 as indicated in FIG. 7*d* by arrow A. Once the stylet tip is pulled out of the narrowed portion 30A of the lumen 30, the whole stylet 44 is much easier to pull out since it is resting rather loosely therein, as explained above, and shown in FIG. 2*b*. The array 10 is curved during this insertion, and so the lumen 30 opens allowing the stylet 44 to be freely removed. Furthermore, the array 10 has now assumed a curved shape similar to the relaxed shape shown in FIG. 2*a*. This causes the lumen 30 to assume a more open shape, which allows the surgical stylet 44 to be easily removed.

Once the surgical stylet 44 is removed, the array 10 relaxes away from the outer wall 45 of the cochlea 48, to reach its final position adjacent to the inner 47 wall of the cochlea and the modiolus. Importantly, the array 10 is in a resting position and is not pressing against the modiolus.

Figure 1B:
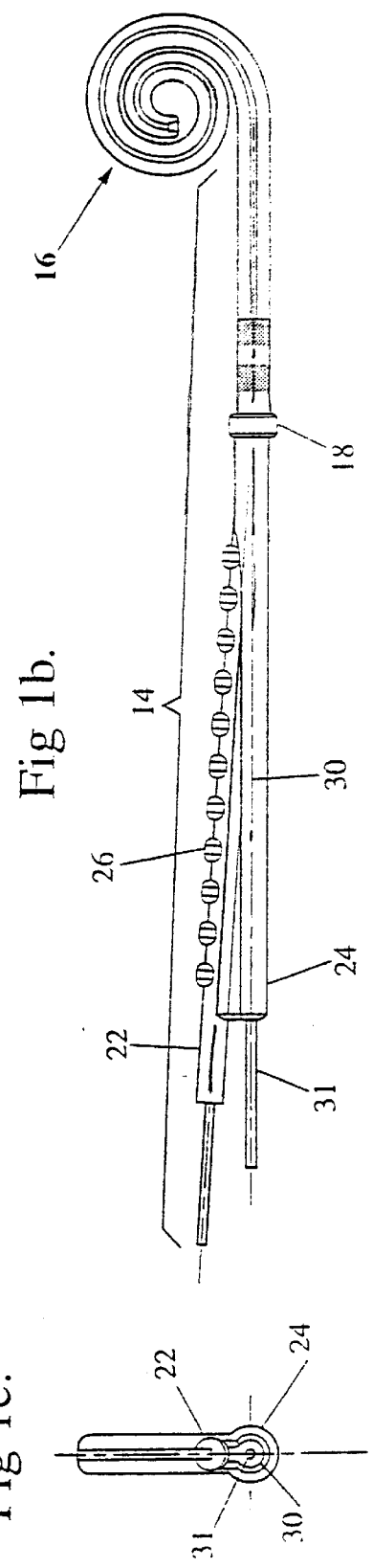

In summary, the electrode array 10 of the present invention is fabricated in a curved shape (FIGS. 1*a* and 1*b*). It has a lumen 30 which allows a surgical stylet 44 to be inserted to hold the array straight for surgical insertion (FIGS. 2*a* and 2*b*). Importantly, the lumen 30 is fabricated so that the opening is almost round when the array 10 is in its relaxed or curved configuration. When the array 10 is straight, the lumen 30 constricts and holds the stylet 44. These features allow the stylet 44 to be withdrawn easily from the lumen 30 of the electrode array 10 after the array 10 has been inserted into the cochlea 48, since the array is curved by contact with the outer wall 45 of the cochlea 48. After the surgical stylet 44 is removed, the array 10 assumes its fully curved shape, and achieves a final position lying close to the modiolus.

Preferably the cross-sectional shape of the electrode carrier is not round, but is approximately square with rounded corners (FIGS. 2*b*, 2*c*). This reduces the possibility that the array 10 will twist during insertion.

The lumen 30 is a dynamic feature in that it changes its shape depending on the curvature of the array 10: when the array 10 is in its curved state the lumen 10 is open and round. When the array 10 in its relaxed curved state (somewhat less curved than the moulded shape) the lumen is open and elliptical in shape.

When the array 10 is straightened, the walls of the lumen 30 collapse closing the lumen 30 such that the surgical stylet 44 is gripped and held in. This ensures that the stylet 44 will not fall out of the lumen during transportation or manipulation prior to surgery as the array is held straight.

During insertion into the cochlea the array becomes partially curved. This causes the lumen to open. After insertion the lumen is open which releases the stylet allowing it to be easily removed.

Figure 4C:
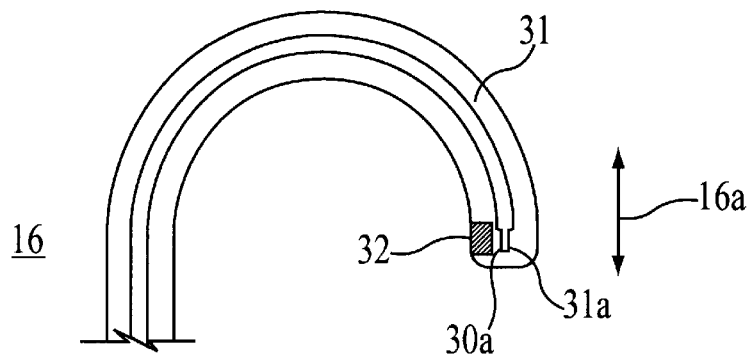
FIG. 4c shows details of the blank tip.

Preferably the lumen is of a reduced diameter for a small distance at its tip (FIG. 4*c*). The surgical stylet is frictionally fit into this reduced diameter section, so that it is firmly held there. Throughout the remainder of the distance of the lumen and stylet the stylet is a loose fit so that it can be easily removed.

Preferably the shaped lumen is fabricated by removing the teflon from the production stylet for a length of 0.15 mm, from the point where the production stylet passes the last electrode. Thus the lumen will be a constant diameter of 0.18 mm until the last 0.15 mm where the diameter will be 0.127 mm. The surgical stylet is 0.125 mm and since neither the lumen nor the stylet are preferably round, there will be a friction fit over the last 0.15 mm. This has the advantage that the surgical stylet is locked into the tip of the electrode array, and the initial force for removal of the stylet is comparatively high. Once the surgical stylet is withdrawn 0.15 mm, however, the stylet is then easily removed. Therefore, the surgical stylet is unlikely to be dislodged accidentally, yet is relatively easy to remove intentionally.

Figure 2D:
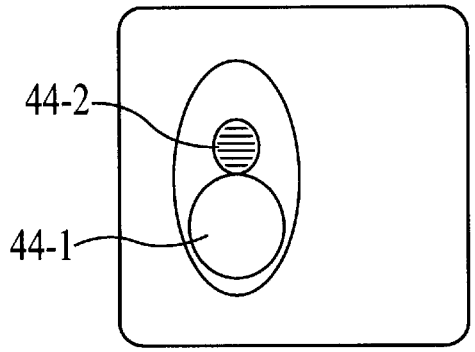
FIG. 2d is similar to FIG. 2b with two surgical stylets.

Preferably the tip of the electrode array is moulded straight, while the remainder of the array is curved. This helps to prevent the array tip from folding over during insertion. The carrier is moulded with a continuing tightening curve until approximately 0.7 mm before the tip. The last 0.7 mm of the electrode is fabricated straight. Because the tip is not predisposed to curving, even if the stylet withdraws slightly during insertion, it would require a large force to be applied during insertion to cause the electrode to double back on itself. In this manner, the surgical stylet 44 has a variable flexibility along its length. In an alternate embodiment two stylets 44-1 and 44-2 may be inserted into lumen 30 with one of them (for instance 44-2) extending only partially along the length of array 10 (as shown in FIG. 2*d*).

Figure 1C:
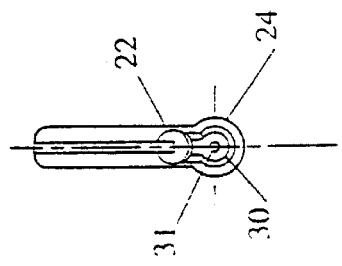
FIG. 1c shows an end elevational view of the electrode array of FIGS. 1a and 1b.

The array shown in FIGS. 1*a*–1*c* could be designed in other ways as well. For example, the array could be moulded from two dies to form two halves which can then be glued together.

Alternatively, the array could be formed in two separate parts—a straight electrode carrier with a channel, and a curved tube. The tube could then be glued into the channel so as to create a curved array with a lumen which is open (round) when the array is in its curved shape.

Obviously, modifications could be made to the invention without departing from its scope as defined in the appended claims. For example, it is possible make and use an array with a stylet without the special shaped lumen.

What is claimed is:

1. A cochlear electrode array kit for stimulating an auditory nerve of a patient, said electrode array kit comprising:
    an elongated carrier arranged and constructed to have a first and a second configuration and having a carrier surface, said electrodes are positioned to apply stimulation to said auditory nerve, and a lumen extending longitudinally through said carrier, said lumen having a cross-sectional dimension which increases as said elongated carrier changes shape from said first to said second configuration to allow said stylet to be withdrawn;
    a plurality of electrodes disposed on said carrier surface; and a plurality of wires connected to said electrodes and embedded in said carrier to provide signals to said electrodes;
    wherein said elongated carrier in said first configuration is insertable into said cochlear and wherein in said second configuration after insertion, said electrodes are positioned to apply stimulation to said auditory nerve; and
    a stylet sized to fit into said lumen and extend substantially through said carrier, said stylet, said wires and said carrier cooperating to change said elongated carrier between said first and second configuration.

2. The cochlear electrode array kit of claim 1 wherein said carrier is biased toward said first configuration when said stylet is inserted into said carrier.

3. The cochlear electrode array kit of claim 1 wherein said elongated carrier is made of a silicone material.

4. The cochlear electrode array kit of claim 1 wherein said stylet is made of a malleable, biocompatible material.

5. The cochlear electrode array kit of claim 4 wherein said malleable, biocompatible material is platinum.

6. The cochlear electrode array kit of claim 1 wherein said stylet includes a tip, said tip being more flexible than the rest of said stylet.

7. The cochlear electrode array kit of claim 1 wherein said elongated carrier includes a tip, said tip being more straight and flexible than the rest of the said elongated carrier.

8. The cochlear electrode array kit of claim 1 wherein said stylet has a variable stiffness.

9. A cochlear electrode array for a cochlear implant comprising:
    elongated carrier having a proximal end and a distal end;
    a plurality of electrodes attached to said elongated carrier, each of said electrodes comprises a ring collapsed to form a U-shaped member; and
    leads connected to said electrodes and extending to said proximal end.

10. The cochlear electrode array of claim 9 wherein each of said electrodes is connected to one of said leads.

11. The cochlear electrode array of claim 9 wherein at least one of said electrodes is connected to at least two of said leads.

12. The cochlear electrode array of claim 9 wherein said elongated carrier has a longitudinal axis and wherein said rings are arranged orthogonally to said longitudinal axis.

13. The cochlear electrode array of claim 12 wherein said electrodes form a channel, said leads being disposed in said channel.

14. The cochlear electrode array of claim 9 wherein said elongated carrier is shaped into a curved configuration to fit inside the cochlea of a person, said cochlea including a modiolus, said elongated carrier having an inner side, said electrodes being oriented on said inner side to face said modiolus when said carrier is inserted into the cochlea.

15. The cochlear electrode array of claim 9, said elongated having an outer side, wherein said outer side is smooth to prevent any damage to the cochlea as said carrier is inserted into the cochlea.

16. A method of making a cochlear electrode array for implantation into the cochlea of a patient as part of a cochlear implant system comprising:
    forming an elongated blank around a curved production stylet;
    removing said curved production stylet to create a lumen through said elongated blank;
    straightening said elongated blank and inserting a straight production stylet into the said lumen;
    attaching electrodes and wires to said elongated blank; and
    withdrawing said straight production stylet.

17. The method of claim 16 further comprising generating each said electrode by the steps of providing a ring of a conductive material, threading one of said wire through said ring and collapsing said rings to grip said one of said wires.

18. The method of claim 17 wherein said step of collapsing includes electrowelding said ring.

19. The method of claim 17 wherein each said ring is collapsed into a U-shaped electrode.

20. The method of claim 19 wherein the said elongated blank is formed with a channel.

21. The method of claim 20 wherein the said wires are placed into the said channel formed in the said elongated blank.

22. The method of claim 21 wherein each of said u-shaped electrodes with its said attached wire is placed one-by-one into said channel starting from the tip of the said elongated blank, such that each electrode covers the wires of the electrodes which have been previously placed on the blank.

23. The method of claim 16 further comprising positioning said blank with said electrodes into a curved die and applying a moulding material to said blank and said electrodes to form a unitary carrier.

24. The method of claim 16 wherein said production stylet is withdrawn from said body first to generate said lumen, said blank is straightened and a second straight stylet inserted to hold said blank in a straight configuration before said electrodes are attached to said blank.

25. A method of making a cochlear electrode array for implantation into the cochlea of a patient as part of a cochlear implant system comprising:
    providing a plurality of electrodes, each electrode being attached to a wire, and being formed by
        providing a plurality of rings;
        welding a wire to each ring; and
        positioning said electrodes in a spaced relationship in a moulding die with said wires extending toward one end of said moulding die; and
    applying a moulding material into said moulding die to form a carrier with said electrodes and wires being embedded in said moulding material.

26. The method of claim 25 further comprising collapsing said electrodes into a U-shaped electrode element.

27. The method of claim 26 further comprising positioning said electrodes in said moulding die to form a channel and positioning said wires in said channel.

28. The method of claim 27 further comprising inserting into said moulding die a production stylet before said moulding materials is applied, and removing said production stylet from said carrier to form a lumen therein.

29. The method of claim 25 further comprising providing said moulding die in a first shape having a first curvature.

30. The method of claim 29 comprising forming the said electrode array such that after straightening said electrode array will relax to a second relaxed curve having a second curvature larger than said first curvature.

31. The method of claim 29 wherein said moulding die is formed with said first curvature smaller than the curvature of the shape of the human cochlea.

32. The method of claim 31 wherein the second relaxed curvature matches the curvature of the human cochlea.

33. A stylet insertion jig, stylet and precurved cochlear electrode array combination for forming a straightened cochlear electrode array, said combination comprising:
- a precurved cochlear electrode array having a longitudinal lumen adapted to receive a stylet;
- an elongated stylet having a long axis;
- a jig including:
  - a chassis upon which is mounted a variable engagement means arranged to position said array and said stylet relative to each other, an end section of said lumen intersecting said long axis of said variable engagement means operative to insert said stylet into said lumen;
  - an electrode array straightening means mounted on said chassis and engaging said array and operative to straighten said array.

34. A combination according to claim 33, wherein said stylet is formed of a malleable material having an annealed tip at a first end and a loop at a second end, said loop forming a means of engagement.

35. A combination according to claim 34, wherein said straightening means cooperates with said variable engagement means to incrementally straighten said precurved electrode array during insertion of said stylet.

36. A stylet insertion jig for straightening a precurved cochlear electrode array having a lumen and for inserting a stylet into said lumen, said jig comprising:
- a chassis upon which is mounted a variable engagement means arranged to position said array and said stylet relative to each other, an end section of said lumen intersecting said long axis of said variable engagement means operative to insert said stylet into said lumen;
- an electrode array straightening means mounted on said chassis and engaging said array and operative to straighten said array.

37. A stylet insertion jig according to claim 36, wherein said straightening means cooperates with said variable engagement means to incrementally straighten said precurved electrode array during insertion of said stylet.

38. A cochlear electrode array kit for stimulating an auditory nerve of a patient, said electrode array kit comprising:
- an elongated carrier having a carrier surface and a lumen extending longitudinally through said carrier;
- a plurality of electrodes disposed on said carrier surface; and a plurality of wires connected to said electrodes and embedded in said carrier to provide signals to said electrodes;
- wherein said elongated carrier is arranged and constructed to have a first configuration in which said carrier is insertable into said cochlea and a second configuration in which after insertion, said electrodes are positioned to apply stimulation to said auditory nerve; and
- a stylet sized to fit into said lumen and extend substantially through said carrier, said stylet, said wires and said carrier cooperating to change said elongated carrier between said first and second configuration, wherein said stylet includes a tip, said tip being more flexible than the rest of said stylet.

39. A cochlear electrode array kit for stimulating an auditory nerve of a patient, said electrode array kit comprising:
- an elongated carrier having a carrier surface and a lumen extending longitudinally through said carrier;
- a plurality of electrodes disposed on said carrier surface; and a plurality of wires connected to said electrodes and embedded in said carrier to provide signals to said electrodes;
- wherein said elongated carrier is arranged and constructed to have a first configuration in which said carrier is insertable into said cochlea and a second configuration in which after insertion, said electrodes are positioned to apply stimulation to said auditory nerve, wherein said elongated carrier includes a tip, said tip being more straight and flexible than the rest of the said elongated carrier, with one of said electrodes being located at said tip; and
- a stylet sized to fit into said lumen and extend substantially through said carrier, said stylet, said wires and said carrier cooperating to change said elongated carrier between said first and second configuration.

40. A cochlear electrode array kit for stimulating an auditory nerve of a patient, said electrode array kit comprising:
- an elongated carrier having a carrier surface and a lumen extending longitudinally through said carrier;
- a plurality of electrodes disposed on said carrier surface; and a plurality of wires connected to said electrodes and embedded in said carrier to provide signals to said electrodes;
- wherein said elongated carrier is arranged and constructed to have a first configuration in which said carrier is insertable into said cochlea and a second configuration in which after insertion, said electrodes are positioned to apply stimulation to said auditory nerve; and
- a stylet sized to fit into said lumen and extend substantially through said carrier, said stylet having a variable stiffness, said stylet, said wires and said carrier cooperating to change said elongated carrier between said first and second configuration.

41. A method of making a cochlear electrode array for implantation into the cochlea of a patient as part of a cochlear implant system comprising:
- providing a plurality of electrodes, each electrode being U-shaped being attached to a wire;
- positioning said electrodes in a spaced relationship in a moulding die to form a channel with said wires extending toward one end of said moulding die through said channel; and
- applying a moulding material into said moulding die to form a carrier with said electrodes and wires being embedded in said moulding material.

42. A method of making a cochlear electrode array for implantation into the cochlea of a patient as part of a cochlear implant system comprising:
- providing a plurality of electrodes, each electrode being attached to a wire;
- positioning said electrodes in a spaced relationship in a moulding die with said wires extending toward one end of said moulding die;
- positioning a production stylet within said moulding die;
- applying a moulding material into said moulding die to form a carrier with said electrodes, wires and said production stylet being embedded in said moulding material; and
- withdrawing said production stylet from said carrier to form a lumen.

* * * * *